United States Patent
Grunze

(10) Patent No.: US 8,007,821 B2
(45) Date of Patent: Aug. 30, 2011

(54) SUBSTRATES CONTAINING POLYPHOSPHAZENE AS MATRICES AND SUBSTRATES CONTAINING POLYPHOSPHAZENE WITH MICROSTRUCTURED SURFACE

(75) Inventor: Michael Grunze, Neckargemünd (DE)

(73) Assignee: CeloNova BioSciences Germany GmbH, Ulm (DE)

( * ) Notice: Subject to any disclaimer, the term of this patent is extended or adjusted under 35 U.S.C. 154(b) by 1137 days.

(21) Appl. No.: 10/250,985

(22) PCT Filed: Jan. 11, 2002

(86) PCT No.: PCT/EP02/00230
§ 371 (c)(1),
(2), (4) Date: Aug. 8, 2003

(87) PCT Pub. No.: WO02/064666
PCT Pub. Date: Aug. 22, 2002

(65) Prior Publication Data
US 2004/0096969 A1 May 20, 2004

(30) Foreign Application Priority Data
Jan. 11, 2001 (DE) .................. 101 00 961

(51) Int. Cl.
A61K 9/14 (2006.01)
A61K 31/74 (2006.01)
A61F 2/00 (2006.01)
A01N 63/00 (2006.01)
A01N 65/00 (2006.01)
C12N 5/00 (2006.01)
C12N 5/02 (2006.01)

(52) U.S. Cl. .................. 424/423; 424/78.08; 424/93.1; 424/486; 435/378; 435/395

(58) Field of Classification Search .................. None
See application file for complete search history.

(56) References Cited

U.S. PATENT DOCUMENTS

| | | | |
|---|---|---|---|
| 4,311,736 A | 1/1982 | Leong | |
| 4,318,947 A | 3/1982 | Joung | |
| 4,341,844 A | 7/1982 | Leong | |
| 4,424,395 A | 1/1984 | Strom | |
| 4,451,647 A | 5/1984 | Allcock et al. | |
| 4,480,642 A | 11/1984 | Stoy et al. | |
| 4,579,880 A | 4/1986 | Ohashi | |
| 4,592,755 A | 6/1986 | Pettigrew et al. | |
| 4,798,876 A | 1/1989 | Gould et al. | |
| 4,883,699 A | 11/1989 | Aniuk et al. | |
| 4,911,691 A | 3/1990 | Aniuk et al. | |
| 5,104,947 A * | 4/1992 | Schacht et al. ................. 525/538 |
| 5,238,569 A | 8/1993 | Soria et al. | |
| 5,548,060 A | 8/1996 | Allcock et al. | |
| 5,605,696 A | 2/1997 | Eury et al. | |
| 5,634,946 A | 6/1997 | Slepian | |
| 5,707,597 A | 1/1998 | Andrianov et al. | |
| 5,788,979 A | 8/1998 | Alt et al. | |
| 5,814,704 A | 9/1998 | Andrianov et al. | |
| 5,873,904 A | 2/1999 | Ragheb et al. | |
| 5,885,829 A * | 3/1999 | Mooney et al. ................. 435/325 |
| 5,914,388 A | 6/1999 | Allcock | |
| 5,980,972 A | 11/1999 | Ding | |
| 5,997,301 A | 12/1999 | Linden | |
| 6,007,573 A | 12/1999 | Wallace et al. | |
| 6,077,916 A | 6/2000 | Laurencin | |
| 6,203,788 B1 | 3/2001 | Blaschuk et al. | |
| 6,235,061 B1 | 5/2001 | Laurencin et al. | |
| 6,254,634 B1 | 7/2001 | Anderson | |
| 6,299,597 B1 * | 10/2001 | Buscemi et al. ......... 604/101.03 |
| 6,319,984 B1 | 11/2001 | Song et al. | |
| 6,432,128 B1 | 8/2002 | Wallace et al. | |
| 6,447,835 B1 * | 9/2002 | Wang et al. .................. 427/2.24 |
| 6,485,514 B1 | 11/2002 | Wrenn, Jr. | |
| 6,503,556 B2 | 1/2003 | Harish et al. | |
| 6,506,411 B2 | 1/2003 | Hunter et al. | |
| 6,548,590 B1 * | 4/2003 | Koloski et al. ................. 524/492 |
| 6,569,195 B2 | 5/2003 | Yang et al. | |
| 6,652,575 B2 | 11/2003 | Wang | |
| 6,808,522 B2 * | 10/2004 | Richards et al. ........... 604/890.1 |
| 2002/0051730 A1 | 5/2002 | Bodnar et al. | |
| 2002/0094440 A1 | 7/2002 | Llanos et al. | |
| 2002/0111590 A1 | 8/2002 | Davila et al. | |
| 2002/0133183 A1 | 9/2002 | Lentz et al. | |
| 2002/0165608 A1 | 11/2002 | Llanos et al. | |
| 2003/0004568 A1 | 1/2003 | Ken et al. | |
| 2003/0065345 A1 | 4/2003 | Weadock | |
| 2003/0065377 A1 | 4/2003 | Davila et al. | |
| 2003/0153985 A1 | 8/2003 | Lee | |
| 2008/0095816 A1 | 4/2008 | Gordy et al. | |

FOREIGN PATENT DOCUMENTS

| | | |
|---|---|---|
| DE | 196 13 048 A | 10/1996 |
| DE | 196 13 048 C2 | 10/1996 |
| DE | 100 19 982 A | 10/2001 |
| DE | 101 00 961 A1 | 8/2002 |
| EP | 0 150 699 A2 | 8/1985 |
| EP | 0 286 709 A1 | 10/1988 |
| EP | 0 804 909 A2 | 11/1997 |

(Continued)

OTHER PUBLICATIONS

Verweire et al, "Fluorinated polymers for bimedical applications", ACS, abstract only 1998.*

(Continued)

*Primary Examiner* — Debbie K Ware
(74) *Attorney, Agent, or Firm* — Rissman Hendricks & Oliverio LLP

(57) ABSTRACT

The invention relates to substrates containing polyphosphazene with a forming surface as matrices for producing biological materials that can be implanted in a mammal. The invention also relates to a method for producing said substrates and substrates containing polyphosphazene with a microstructured surface.

12 Claims, No Drawings

FOREIGN PATENT DOCUMENTS

| | | |
|---|---|---|
| EP | 1 112 094 B1 | 7/2001 |
| EP | 1 179 353 A1 | 2/2002 |
| JP | 58-079915 A | 5/1983 |
| WO | WO 93/21858 A1 | 11/1993 |
| WO | WO 95/02628 A1 | 1/1995 |
| WO | WO 96/00103 A1 | 1/1996 |
| WO | WO 96/04015 A1 | 2/1996 |
| WO | WO 96/25897 A2 | 8/1996 |
| WO | WO 9831734 A1 | 7/1998 |
| WO | WO 98/52605 A1 | 11/1998 |
| WO | WO 98/56312 A1 | 12/1998 |
| WO | WO 99/09088 A | 2/1999 |
| WO | WO 99/16416 A2 | 4/1999 |
| WO | WO 99/16477 A2 | 4/1999 |
| WO | WO 99 45096 A | 9/1999 |
| WO | WO 99/45096 A1 | 9/1999 |
| WO | WO 99/52356 A1 | 10/1999 |
| WO | WO 00/61204 A1 | 10/2000 |
| WO | WO 01/45763 A1 | 6/2001 |
| WO | WO 01/70296 A1 | 9/2001 |
| WO | WO 01 80919 A | 11/2001 |
| WO | WO 01/80919 A1 | 11/2001 |
| WO | WO 02/24247 A1 | 3/2002 |
| WO | WO 02077073 A2 | 10/2002 |
| WO | WO 03/015719 A1 | 2/2003 |

OTHER PUBLICATIONS

Laurencin C.T. et al., "Use of polyphosphazenes for skeletal tissue regeneration," Journal of Biomedical Materials Research, Bd. 27, Nr. 7, 1993, pp. 963-973. XP008004104.

A. Welle et al. Blood Compatibility of Poly[bis(trifluoroethoxy)phosphazene], Institute of Applied Physical Chemistry, JAMP, vol. 4, 6-10 (2000), University of Heidelberg, Germany.

A. Welle et al., "Polyphosphazenes as Antithrombotic Coatings for Prosthetic Heart Valves," Presented at 19 Annual Meeting of the Adhesion Society, Myrtle Beach, SC, 4 pages (Feb. 1996).

C.T. Laurencin et al., "Use of polyphosphazenes for skeletal tissue regeneration," J. Biomedical Materials Research, vol. 27, No. 7, pp. 963-973 (1993), John Wiley & Sons, Inc., USA.

F. Veronese et al., "Polyphosphazene Membranes and Microspheres in Periodontal Diseases and Implant Surgery," Biomaterials, vol. 20, 91-98 (1999), Elsevier, USA.

G. Lopez et al., "Glow Discharge Plasma Deposition of Tetraethylene Glycol Dimethyl Ether for Fouling-Resistant Biomaterial Surfaces," J. of Biomedical Materials Research, vol. 26, 415-439 (1992), John Wiley & Sons, Inc., USA.

H. Allcock et al., "Antibacterial activity and mutagenicity studies of water-soluble phosphazene high polymers," Biomaterials, vol. 13, No. 2, pp. 847-862 (1992), Butterworth-Heinemann Ltd., USA.

H. Allcock, "Polyphosphazenes," Inorganic Polymers, pp. 61-139 (1992).

I. De Scheerder et al., "Angiopeptin Loaded Stents Inhibit the Neointimal Reaction Induced by Polymer Coated Stents Implanted in Porcine Coronary Arteries," Abstract 772-6, pp. 286A, J ACC (Feb. 1995). (Abstract).

M. Kajiwara, "The Study of the Cultivation of Chinese Hamster Ovary and Bows Cell Lines," Phosphorus, Sulfur, and Silicon, vol. 76, pp. 163-166 (1993), Gordon and Breach Science Publishers S.A., USA.

P. Kingshott, "Surfaces that Resist Bioadhesion," Current Opinion in Solid State and Materials Science, vol. 4, 403-412 (1999), Pergamon.

Ph. Potin & R. DeJaeger, "Review: Polyphosphazenes: Synthesis, Structures, Properties, Applications," European Polymer Journal, vol. 27, 341-348 (1991), Pergamon Press, Great Britain.

R. De Jaeger & M. Gleria, "Poly(organophosphazene)s and Related Compounds: Synthesis, Properties and Applications," Prog. Polym. Sci., vol. 23, 179-276 (1998), Pergamon Press, Great Britain.

R. Waksman, "Vascular Brachytherapy: Applications in the Era of Drug-Eluting Stents," Reviews in Cardiovascular Medicine, vol. 3, S23-S30 (2002), MedReviews, LLC, USA.

R.R. McCaffrey et al., "Synthesis, Casting, and Diffusion Testing of Poly[bis(tri-fluoroethoxy)phosphazene] Membranes," J. of Membrane Science, vol. 28, 47-67 (1986), Elsevier Science Publishers B.V., Netherlands.

S. Cohen et al., "Design of Synthetic Polymeric Structures for Cell Transplantation and Tissue Engineering," Clinical Materials, vol. 13, 3-10 (1993), Elsevier Science Publishers Ltd, England.

S. Ibim et al., "Controlled Macromolecule Release from Poly(phosphazene) Matrices," J. of Controlled Release, vol. 40, 31-39 (Jun. 1996), Elsevier Science B.V. (Abstract).

S. Vinogradova et al., "Open-chain Poly(organophosphazenes). Synthesis and Properties," Russian Chemical Reviews, vol. 67, 515-534 (1998), Russian Academy of Sciences and Turpion Ltd.

V. Korsak et al., "On the Effect of Water on the Polymerization of Hexachlorocyclotriphosphazenes," Acta Polymerica, vol. 30, No. 5, 245-248 (1979).

Y. Lemmouchi et al., "Biodegradable Polyphosphazenes for Drug Delivery," Macromolecular Symposia, vol. 123, 103-112 (Sep. 1997) Wiley VCH, Weinheim, Germany.

E.W. Barrett, E.A., "Patterning Poly(organophosphazenes) for Selective Cell Adhesion Applications", Biomacromolecules, 2005, vol. 6, 1689-1697.

* cited by examiner

SUBSTRATES CONTAINING POLYPHOSPHAZENE AS MATRICES AND SUBSTRATES CONTAINING POLYPHOSPHAZENE WITH MICROSTRUCTURED SURFACE

This application was filed under 35 U.S.C. 371 as a national stage of PCT/EP02/00230, filed Jan. 11, 2002; and which claims priority to German Application No. 101 00 961.5, filed Jan. 11, 2001, respectively.

The present invention concerns substrates containing polyphosphazene with a forming surface as matrices for producing biological materials that can be implanted in a mammal, a process for producing such substrates, and substrates containing polyphosphazene with microstructured surfaces.

Culturing of cells, especially of endothelial cells, with the goal of growing artificial organs, is a comparatively new development in implantology. One particular advantage of this technology is that implants prepared in this manner are expected to exhibit complete compatibility with the body. Given that cell collections cultured ex vivo initially do not have either the shape or the mechanical stability desired for the later implants, such as organs, arteries, etc., such implants are initially preformed on a forming substrate. Examples of substrates currently used, on which such cells are cultured, and which are the primary supporting structure for such an implant, include polylactides, polyethylene glycols, polyurethanes, Teflon, and inorganic substrates.

Numerous other materials being used to produce such primary supporting structures or supporting substrates are known from the prior art and are being investigated. For example, an expandable shell of ε-PTFE, which can also be used for the culturing of artificial blood vessels, is known from WO 98/56312. Other materials for this application are described in EP-A-0 810 845, U.S. Pat. No. 4,883,699, and U.S. Pat. No. 4,911,691. Examples of other polymers for this purpose include hydrolyzed polyacrylonitrile (U.S. Pat. No. 4,480,642), hydrophilic polyethers (U.S. Pat. No. 4,798,876) and polyurethane diacrylates (U.S. Pat. No. 4,424,395). Also, various hydrogels are known that can be used as coatings for this purpose. The group of potentially applicable materials can also be supplemented by polyvinylpyrrolidone (PVP), polyvinyl alcohols (PVA), polyethylene oxide (PEO) and polyhydroxyethyl methacrylate p(HEMA). Furthermore, use of a group of standard materials such as polyurethanes, polyethylenes and polypropylenes is also described in the prior art as possible materials for such substrates. Mixtures of these materials with one another are also known. Another group of materials is known from EP-A-0 804 909.

Given that the inherent characteristics of these materials differ, it can be assumed that each of these materials, or each of these substances, exhibits special characteristics for certain applications in the culture of artificial implants. For instance, PVA dissolves very well in liquid and is rapidly absorbed. Other materials exhibit good compatibility with blood. Still other materials are particularly extensible. Unfortunately, however, all materials have drawbacks in various areas. For instance, PVA does not exhibit particularly good blood compatibility.

ε-PTFE, for instance, is quite extensible and also exhibits good blood compatibility; but this material is very difficult to handle and production of supporting substrates from this material requires a series of specific processing steps (see WO 96/00103). The surface of the ε-PTFE substrate obtained in that manner is also very porous, so that cells grow into this material very strongly and it is almost impossible to avoid damage when separating the cultured cell material for an implant from the supporting substrate. For other materials, elastic properties, which are important for such a supporting substrate in some cases, can be achieved only by adding plasticizers which reduce compatibility with the blood and body, and which also present an undesirable affect on the cell culture due to bleeding of the "plasticizers".

The greatest difficulties that arise in the culturing of cells for implants are reactions with the supporting substrate or with its degradation products. It is known, for example, that inflammatory reactions can occur in recipients due to the dissolving or absorption and decomposition of some of the substances known in the state of the art (van der Gießen, Circulation, Volume 94, No. 7, 1996). Those arise either because of partially incomplete compatibility of such supporting substrates, or because of reaction with decomposition products that arise due to decomposition of the substances noted. Furthermore, cracks and fractures can occur in the freshly cultured implant when the cultured implant is to be removed from the supporting substrate. That disadvantageous effect is primarily due to the fact that the cells growing for the implant bind very tightly to the supporting substrate, particularly so with polylactide, for example; because of the pore structure that arises from dissolution or due to the basic surface nature of the supporting substrate, they intertwine with the supporting substrate so that it is practically impossible to remove them without damage.

Behavior with respect to bacteria and proteins that are deposited on the surfaces of the supporting substrate is also a major factor in the successful culturing of the implants noted, cells in particular, because these deposits can lead to significant inflammations in patients and to other problems with the growth and culture of the cells.

The cracks that have been mentioned, which can occur on removal of cultured blood vessel implants from the supporting substrate, are an important aspect in the production of vascular implants. These cracks are, for instance, points of attachment for increased development of thrombi in recipients or patients, and for other deposits (proteins, macrophages, etc.) that can become a risk for the recipients or patients after implantation.

Thus the present invention is based on the objective of providing a new system for producing implants from biological materials that is intended to allow the most selective growth possible of the desired cells and to assure essentially damage-free separation of implants made of the desired cells from the supporting substrate used.

This objective is achieved by the embodiments as characterized in the claims. In particular, the use of a substrate with a forming (or form building) surface is provided, comprising at least partially a biocompatible polymer with the following general formula (I)

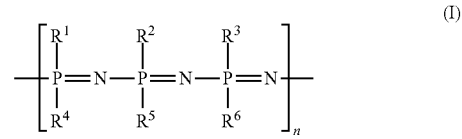

in which n stands for 2 to ∞, $R^1$ to $R^6$ are the same or different and stand for an alkoxy, alkylsulfonyl, dialkylamino or aryloxy group, or a heterocycloalkyl or heteroaryl group having nitrogen as the hetero atom, as a matrix for producing biological material that can be implanted in a mammal.

In one preferred embodiment of the present invention, the biocompatible polymer according to Formula (I) is provided as a coating on the substrate to develop the forming surface. In this embodiment of the invention, there is no particular limitation on the substrate used, and it can be any material, such as plastics, metals, metal alloys and ceramics. The biocompatible coating has, for example, a thickness from about 1 nm up to about 1000 µm, preferably up to about 10 µm, and especially preferably up to about 1 µm. In another preferred embodiment of the present invention the substrate having a forming surface is a shaped object or moulding or moulded article made of the biocompatible material according to Formula (I).

The degree of polymerization of the biocompatible polymer according to Formula (I) is preferably in a range of 20 to 200,000, more preferably from 40 to 100,000.

Preferably at least one of the groups $R^1$ to $R^6$ in the polymer used is an alkoxy group, substituted with at least one fluorine atom.

The alkyl groups in the alkoxy, alkylsulfonyl and dialkylamino groups are, for example, straight-chain or branched-chain alkyl groups with 1 to 20 carbon atoms, wherein the alkyl groups can, for example, be substituted by at least one halogen atom, such as a fluorine atom.

Examples of alkoxy groups are methoxy, ethoxy, propoxy and butoxy groups, which can preferably be substituted by at least one fluorine atom. The 2,2,2-trifluoroethoxy group is particularly preferred. Examples of alkylsulfonyl groups include methylsulfonyl, ethylsulfonyl, propylsulfonyl and butylsulfonyl groups. Examples of dialkylamino groups include dimethylamino, diethylamino, dipropylamino and dibutylamino groups.

The aryl group in the aryloxy group is, for example, a compound with one or more aromatic ring systems, in which the aryl group can, for example, be substituted with at least one alkyl group as defined above. Examples of aryloxy groups are phenoxy and naphthoxy groups and derivatives thereof.

An example of the heterocycloalkyl group is a ring system containing 3 to 7 atoms, with at least one ring atom being a nitrogen atom. The heterocycloalkyl group can, for instance, be substituted with at least one alkyl group as defined above. Examples of heterocycloalkyl groups include piperidinyl, piperazinyl, pyrrolidinyl, and morpholinyl groups and their derivatives. The heteroaryl group is, for example, a compound with one or more aromatic ring systems, in which at least one ring atom is a nitrogen atom. The heteroaryl group can, for example, be substituted with at least one alkyl group as defined above. Examples of heteroaryl groups include pyrrolyl, pyridinyl, pyridinolyl, isoquinolinyl and quinolinyl groups and their derivatives.

In another preferred embodiment of the invention, a layer containing an adhesion promoter is placed between the surface of the substrate and the biocompatible coating made of the polyphosphazene derivative.

The adhesion promoter, or spacer, preferably contains a polar end group. Examples of those include hydroxy, carboxy, carboxyl, amino or nitro groups. End groups of the O-ED type can also be used, in which O-ED means an alkoxy, alkylsulfonyl, dialkylamino or aryloxy group, or a heterocycloalkyl or heteroaryl group having nitrogen as a hetero atom, which can be variously substituted, for instance by halogen atoms, especially fluorine.

In particular, the adhesion promoter can, for example, be an organosilicon compound, preferably an amino-terminated silane or one based on aminosilane, amino-terminated alkenes, nitro-terminated alkenes and silanes or an alkylphosphonic acid. Aminopropyltrimethoxysilane is particularly preferred.

The adhesion promoter in particular improves the adhesion of the coating to the surface of the substrate by coupling of the adhesion promoter to the surface of the substrate, through ionic and/or covalent bonds, for example, and by further coupling of the adhesion promoter to the described polymer of Formula (I) of the coating, for instance, through ionic and/or covalent bonds.

The term "biological material" includes, for example, eucaryotic cells, monolayer or multilayer cellular aggregations, tissues, or cell components of mammals, especially of human origin. In one preferred embodiment the donor of the biological starting material is identical to the recipient of the implantable biological material. Examples of the biological starting material or biological material include endothelial cells of various origins (e.g., from skin, foreskin, blood vessels such as the aorta, fatty tissues, eye, omentum, umbilical cord, varices, or the like), epithelial cells of various origins (e.g., from the stomach, intestine, or the like), bone cells, cartilage cells, and all adherent cells or cells in which adherence is inducible, cell aggregations or tissues (e.g., artificial cultured skin or similar tissue), natural tissues, proteins, sugar molecules and lipids. Artificial organs, blood vessels, bones, cartilage, myelin sheaths, etc., can be produced by using the substrate with a forming surface.

A further object of the present invention concerns a process for producing the substrates with forming surface as defined above; wherein the application of a coating of the biocompatible polymer according to Formula (I) to the surface of a shaping body, moulding (or moulded article) or supporting substrate is known from the prior art.

For example, the substrate with a forming surface can be produced according to a preferred embodiment, in general, by the following steps:

(a) A solution containing at least one compound of the general Formula (I) at a concentration of 0.1%-99% is prepared in a solvent that is organic and polar. Ethyl acetate, acetone, THF, toluene, or xylenes, for example, can be used here as solvents. Mixtures of these solvents are also usable, or they can be supplemented by other solvents. This solution is applied to a substrate that exhibits little if any adhesion to the polymer, such as glass, silicon, various ceramics or other appropriate materials such as polymers (PDMS, Teflon, PMMA, polycarbonate or silicone). The surfaces of the substrates listed can also be chemically modified, for instance, by introducing certain functional groups (—$NH_2$, —OH, —COOH, —COH, —COOMe, —$CF_3$, etc.).

(b) Evaporation of the solvent can proceed without further measures; but in the best case the concentration of the solvent vapor over the substrate is controlled, as are the pressure and the temperature. At the beginning of the first phase of drying, the atmosphere over the coated substrate should be saturated with solvent vapor, with the concentration of the solvent vapor then being reduced slowly over many hours. The temperature can vary from −30° C. to +90° C. The pressure can follow a gradient from normal pressure to water aspirator vacuum (20 Torr) during the first phase of drying. After the first phase of drying, the coated substrate is further dried for a certain period at oil pump vacuum (0.1 Torr).

The substrate coated with the biocompatible polymer according to Formula (I) can then be used directly, without or after appropriate sterilization. Various coating thicknesses from 0.1 µm to 300 µm or thicker, preferably in the range from 0.5 µm to 30 µm, and especially preferably about 5 µm, are obtained, depending on the concentration of the polymer solution and the conditions used during the first phase of drying.

Another object of the present invention concerns a substrate with a microstructured surface comprising at least partly a biocompatible polymer according to Formula (I) as defined above, with the size or magnitude of the surface structures being in the range of nanometers, micrometers, or even larger or smaller, preferably in the range of 10 nm to 100 µM. In one preferred embodiment the biocompatible polymer is present on the substrate as a coating with an externally microstructured surface.

The structuring of the surface is not subject to any particular limitation. For instance, all structures that can be generated photolithographically, with an electron beam, with an ion beam, with a laser, or by other techniques, can be produced. The microstructuring of the surface of the substrate or of the coating can also be obtained by "fusion structuring or melt structuring", in which a thin wire is brought to the melting temperature of the biocompatible polymer and then melts the desired structure into the surface of the coating by direct contact.

Special advantages can be attained by means of this structuring with structures that affect the flow behavior of liquids particularly favorably (e.g., sharkskin or lotus effect) imprinted into the surface of the coating or substrate.

The invention claimed is:

1. A method for producing an implantable biological material, the method comprising:
   providing a form-building surface of a substrate;
   disposing a polymer of general formula (I) to form a biocompatible coating layer, at least partially, above the form-building surface of the substrate;
   contacting donor cells of a biological starting material with the biocompatible coating layer to promote the formation of cellular aggregations of the biological starting material above the biocompatible coating layer; and
   detaching in vitro the cellular aggregations of the biological starting material from the biocompatible coating layer to produce the implantable biological material,
   wherein the general formula (I) is

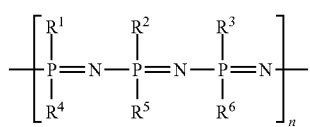

wherein n is 2 to ∞, and
wherein $R^1$ to $R^6$ are the same or different and represent a group selected from the group consisting of an alkoxy, an alkylsulfonyl, a dialkylamino, an aryloxy, a heterocycloalkyl having nitrogen as a heteroatom, and a heteroaryl having nitrogen as a heteroatom.

2. The method of claim 1 further comprising disposing an adhesion promoter above the form-building surface and below the biocompatible coating layer.

3. The method of claim 2, wherein the adhesion promoter is aminopropyltrimethoxysilane.

4. The method of claim 1, wherein the contacting further comprises contacting the donor cells with the biocompatible coating layer comprising the polymers of general formula (I), wherein the biocompatible coating layer has a microstructured surface.

5. The method of claim 4, wherein the biocompatible coating layer is micro-structured to exhibit surface structures of magnitude in the range of 10 nm to 100 µm.

6. The method of claim 1, wherein the biocompatible coating layer has a thickness from 1 nm to 1000 µm.

7. The method of claim 1, wherein the alkoxy group is substituted by at least one fluorine atom.

8. The method of claim 1, wherein the polymer is poly[bis(trifluoroethoxy)phosphazene].

9. The method of claim 1, wherein the substrate is selected from the group consisting of glass, silicon, ceramics, polymers, metals, metal alloys, plastics, and combinations thereof.

10. The method of claim 1, wherein the substrate is chemically modified to introduce functional groups.

11. The method of claim 1, wherein the biological material is selected from the group consisting of eucaryotic cells, monolayer cellular aggregations, multilayer cellular aggregations, endothelial cells from skin, endothelial cells from blood vessels, epithelial cells from stomach, epithelial cells from intestine, bone cells, cartilage cells, myelin sheaths, and components thereof.

12. The method of claim 1, wherein the biological implant is selected from the group consisting of an artificial organ, an artificial blood vessel, an artificial bone, an artificial cartilage, and an artificial myelin sheath.

* * * * *